United States Patent
Ellis et al.

(10) Patent No.: US 11,576,994 B1
(45) Date of Patent: Feb. 14, 2023

(54) GAS IRRADIATION APPARATUS AND METHOD

(71) Applicants: Stanley W. Ellis, Bakersfield, CA (US); Mitchell Caughron, Bakersfield, CA (US)

(72) Inventors: Stanley W. Ellis, Bakersfield, CA (US); Mitchell Caughron, Bakersfield, CA (US)

(*) Notice: Subject to any disclaimer, the term of this patent is extended or adjusted under 35 U.S.C. 154(b) by 0 days.

(21) Appl. No.: 17/841,463

(22) Filed: Jun. 15, 2022

(51) Int. Cl.
| | |
|---|---|
| A61L 9/20 | (2006.01) |
| A62B 9/00 | (2006.01) |
| A62B 18/08 | (2006.01) |
| A62B 18/00 | (2006.01) |

(52) U.S. Cl.
CPC .................. *A61L 9/20* (2013.01); *A62B 9/00* (2013.01); *A62B 18/08* (2013.01); *A61L 2209/12* (2013.01); *A62B 18/006* (2013.01)

(58) Field of Classification Search
CPC .............. A61L 9/20; A62B 9/00; A62B 18/08
See application file for complete search history.

(56) References Cited

U.S. PATENT DOCUMENTS

| | | | |
|---|---|---|---|
| 6,623,544 B1 | 9/2003 | Kaura | |
| 6,983,745 B2 | 1/2006 | Tang et al. | |
| 9,260,323 B2 | 2/2016 | Boodaghians et al. | |
| 10,888,721 B2 | 1/2021 | Hur et al. | |
| 11,033,644 B2 | 6/2021 | Wu et al. | |
| 11,305,032 B2 | 4/2022 | Ellis et al. | |
| 2006/0231100 A1 | 10/2006 | Walker et al. | |
| 2007/0101867 A1 | 5/2007 | Hunter et al. | |
| 2007/0102280 A1 | 5/2007 | Hunter et al. | |
| 2007/0181509 A1* | 8/2007 | Araiza | B01D 53/007 250/435 |
| 2010/0132715 A1 | 6/2010 | Litz | |
| 2011/0114546 A1 | 5/2011 | Barsky et al. | |
| 2012/0299456 A1 | 11/2012 | Horng | |
| 2013/0128561 A1 | 5/2013 | Thomas et al. | |
| 2013/0307549 A1 | 11/2013 | Liu | |

(Continued)

FOREIGN PATENT DOCUMENTS

| | | |
|---|---|---|
| JP | 2020044301 A | 3/2020 |
| WO | WO2020035666 A1 | 2/2020 |

*Primary Examiner* — Kevin Joyner
(74) *Attorney, Agent, or Firm* — James M. Duncan; Scanlon Duncan LLP

(57) ABSTRACT

A gas irradiation system has an irradiation chamber having a plurality of irradiation compartments disposed circumferentially about a central axis. One of the compartments is an inlet compartment. The inlet compartment has an aperture at the bottom through which gas flows from the compartment. A UV LED is disposed within or adjacent to the aperture, where the UVC LED is configured to irradiate the gas and neutralize pathogens. Circumferentially adjacent to one side of the inlet irradiation compartment is an outlet irradiation compartment. Circumferentially adjacent in the opposite circumferential direction on the other side of the inlet radiation compartment is the first of a plurality of intermediate irradiation compartments. These intermediate compartments extend circumferentially about the central axis between the inlet compartment and the outlet compartment. The gas flows sequentially through each of the irradiation compartments, being irradiated in each compartment.

20 Claims, 13 Drawing Sheets

(56) References Cited

U.S. PATENT DOCUMENTS

| | | |
|---|---|---|
| 2014/0264072 A1 | 9/2014 | Abbott et al. |
| 2016/0339133 A1 | 11/2016 | Lichtblau |
| 2017/0007385 A1 | 1/2017 | Wang |
| 2018/0028846 A1 | 2/2018 | Hur et al. |
| 2018/0104374 A1 | 4/2018 | Kim et al. |
| 2018/0250430 A1 | 9/2018 | Machovina et al. |
| 2020/0339441 A1 | 10/2020 | Wu et al. |
| 2021/0206664 A1 | 7/2021 | Bilenko et al. |
| 2021/0260559 A1 | 8/2021 | Yamazaki et al. |

* cited by examiner

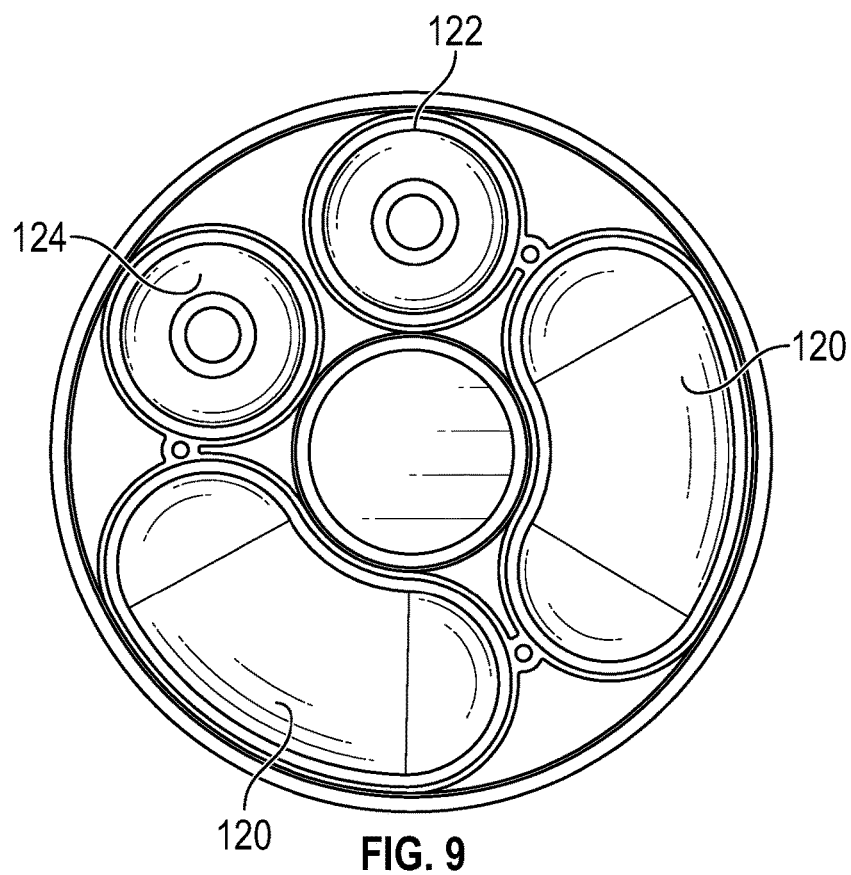
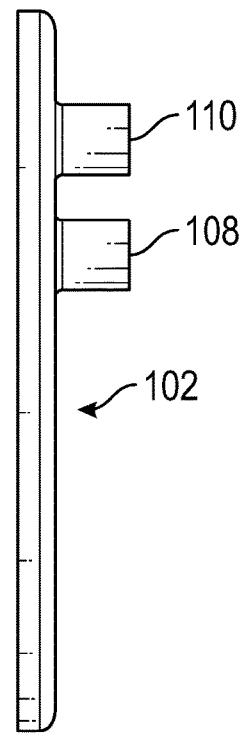
FIG. 9  FIG. 10
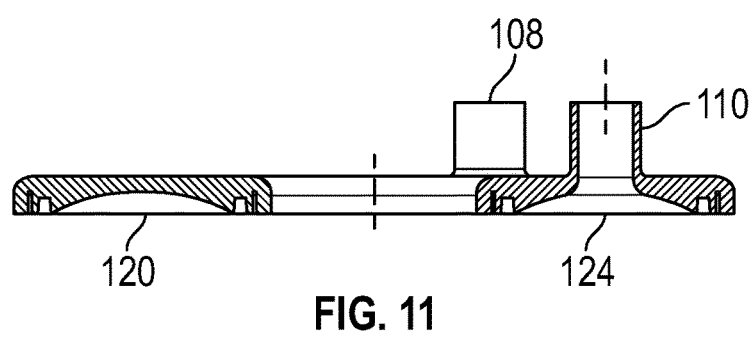
FIG. 11

GAS IRRADIATION APPARATUS AND METHOD

BACKGROUND OF THE INVENTION

The present invention generally relates to the treating gas to neutralize pathogens contained in the gas. More specifically, embodiments of the present invention relate to the neutralizing of pathogens contained in air inhaled by humans. Embodiments of the present invention may also be utilized for treating the exhalations of persons who may be infected with pathogens, including viruses, bacteria, fungi or other pathogens, where the exhalations may otherwise present a potential risk of harm to persons exposed to the exhalations. The recent and ongoing SARS-CoV-2 coronavirus epidemic has illustrated the need for effective devices and methods which can provide safe breathing air for first responders, caregivers, and essential personnel. Such devices are preferably configured into a package which is relatively small, lightweight, easy to use, and having self-contained power means.

UVC light technology ("UV-C light") is a radiation method which makes use of specific wavelengths of ultraviolet light to neutralize pathogens. The wavelengths of UV-C light range from 200 to 300 nanometers. UV-C light is germicidal, which means it deactivates the DNA of microorganisms such as bacteria, viruses, and other pathogens, which disrupt the ability of the microorganisms to multiply and cause disease.

A variety of devices are known which utilize UV-C light for neutralizing pathogens. It is known that the level of neutralization of the pathogens is related to the exposure time of the pathogens to the UV-C light, and the distance of the UV-C light to the pathogens. An apparatus which provides effective exposure time and distance to multiple sources of UV-C light to a gas stream potentially carrying pathogens is desirable. It is also desirable that embodiments of such an apparatus be configured into a portable, lightweight, and self-contained system which may easily be carried and/or worn by first responders, caregivers, essential personnel, etc. It would also be desirable to have a device which may also be configured to neutralize pathogens in the exhalations of an infected person, effectively quarantining the infected person from caregivers, family members and the like. Embodiments of the present invention provide an answer to these needs.

SUMMARY OF THE INVENTION

Embodiments of the presently disclosed gas irradiation system may purify incoming gas streams of pathogens and other biological material by utilizing UV LEDs. The UV LEDs have germicidal wavelengths of 100-400 nm, and typically in the range of 100-280 nm. In some embodiments of the ultraviolet air irradiation units an incoming air stream is first filtered of air particulates, gases, vapors, and/or biological material by passing air through a high efficiency particulate air ("HEPA") filter to screen out particulates, gases, and vapors in addition to the pathogens.

An embodiment of the presently disclosed air irradiation system has an irradiation chamber comprising a plurality of irradiation compartments disposed circumferentially about a central axis. Each irradiation compartment has a top end and a bottom end. One of the compartments of the plurality of irradiation compartments is an inlet compartment. An inlet to the inlet compartment provides a conduit for a flow of a gas into the top end of the inlet irradiation compartment. It is to be appreciated that because the apparatus is capable of reverse flow through the plurality of irradiation compartments, when the flow direction is reversed the "inlet" irradiation compartment will function as the "outlet" irradiation compartment and the "inlet" will function as an "outlet".

The bottom end of the inlet irradiation compartment has an aperture through which the flow of gas exits the inlet irradiation compartment (or the flow of gas enters the compartment in the case of reverse flow). A UV LED having a germicidal wavelength of 100-400 nm, typically in the range of 100-280 nm, is disposed within or adjacent to the aperture, wherein the UV LED is configured to irradiate the flow of gas passing through the aperture. Circumferentially adjacent on one side of the inlet irradiation compartment is an outlet irradiation compartment. Circumferentially adjacent in the opposite circumferential direction on the other side of the inlet radiation compartment is the first of a plurality of intermediate irradiation compartments. These intermediate irradiation compartments extend circumferentially about the central axis between the inlet irradiation compartment and the outlet irradiation compartment.

All of the irradiation compartments (inlet, outlet, and intermediate) have an open upper end and a bottom end. The bottom end of each irradiation compartment is sealed except for an aperture set within the bottom end. A UV LED having a germicidal wavelength of 100-400 nm, typically in the range of 100-280 nm, is disposed within or adjacent to each of the apertures, wherein the UV LED is configured to irradiate the flow of gas passing through the irradiation compartment. In some embodiments the UV LEDs may be connected to a controller which energizes selected UV LEDS according to the irradiation requirements of the particular gas flowing through the irradiation chamber. In some embodiments an optional UVC transparent glass lens, such as one fabricated from quartz, may be placed over each UV LED.

A top cover or comparable structure seals over the top ends of the irradiation compartments. The top cover has an underside having flow channels which provide for gas flow between the top ends of some pairs of adjacent irradiation compartments. Each flow channel may include an O-ring seal which encloses the flow channel to prevent intrusion of gas from other sources and to prevent release of gas from within the flow channel.

A bottom member seals over the bottom ends of the irradiation compartments, wherein the bottom member has an upper side which seals flow channels between the bottom ends of adjacent irradiation compartments. These flow channels may also utilize O-rings to prevent contamination or gas release.

Gas flow through the irradiation compartments may be driven by a pressure differential apparatus. In one embodiment of the apparatus, the pressure differential apparatus is a fan which is disposed upstream of the inlet irradiation chamber. Alternatively, the pressure differential apparatus may be a vacuum fan attached to the outlet irradiation chamber. A HEPA filter may be disposed upstream of the inlet irradiation chamber. For example, a positive pressure fan and filter may be placed immediately upstream of the inlet to the inlet irradiation compartment. Alternatively, a filter may be placed immediately upstream of the inlet to the inlet irradiation compartment and a vacuum plan connected to the outlet of the outlet irradiation compartment.

In a normal flow operation, a flow of gas flows into and through the inlet irradiation compartment and exits the inlet irradiation compartment through the aperture at the bottom end. The flow of gas is irradiated by a first UV LED as it flows through the inlet irradiation compartment. Upon exiting the inlet irradiation compartment, the flow of gas passes through a flow channel between the bottom of the inlet irradiation compartment and a first intermediate irradiation compartment, where the flow channels is sealed by the O-rings and structures of the bottom member. The flow of gas passes from the bottom to the top of the first intermediate irradiation compartment, being irradiated by a second UV LED as it flows. The flow of gas passes through the top end of the first intermediate irradiation compartment through an upper flow path into the top of a circumferentially adjacent second intermediate irradiation compartment where the flow of gas is irradiated by a third UV LED. Flow through the irradiation chamber proceeds sequentially through each of the circumferentially adjacent intermediate irradiation compartments, where irradiation may be applied at each of the intermediate irradiation compartments, until the gas flows into the outlet irradiation compartment through the aperture at the bottom end of the outlet irradiation compartment and exits the irradiation chamber through the outlet at the upper end.

A reverse flow operation may be achieved by changing the direction of a fan or other pressure differential apparatus. In the reverse flow operation, the flow of gas enters the irradiation chamber through the outlet irradiation compartment, flows sequentially through the intermediate irradiation compartments in the same manner as discussed above, enters the inlet irradiation compartment at the aperture at the bottom end and exits the irradiation compartment through the "inlet" at the upper end.

The UV LEDs may be attached to the bottom member. The bottom member may also comprise a heat sink to dissipate the heat generated from the UV LEDS. A heat dissipation fan may be attached to the bottom member to further provide for cooling of the UV LEDs.

Each of the irradiation compartments may be in a cylindrical configuration and the irradiation chamber itself may be cylindrical. The irradiation compartments may be circumferentially disposed about a cylindrical storage compartment. A power source, such as a rechargeable battery, may be disposed within the cylindrical storage compartment. The UV LEDs, heat dissipation fan and the pressure differential apparatus may receive power from the power source.

The air irradiation system may further comprise a tube connected to the outlet irradiation compartment and a face mask attached to the tube. The air irradiation system may be packaged in an easily transportable carrying case for personal usage.

BRIEF DESCRIPTION OF THE DRAWINGS

FIG. 9 depicts a bottom view of the cover for the irradiation chamber depicted in FIG. 7.

FIG. 10 shows a side view of the cover for the irradiation chamber depicted in FIG. 7.

FIG. 11 depicts a sectional view taken along line 11-11 of FIG. 8.

DETAILED DESCRIPTION OF THE INVENTION

Figure 1:
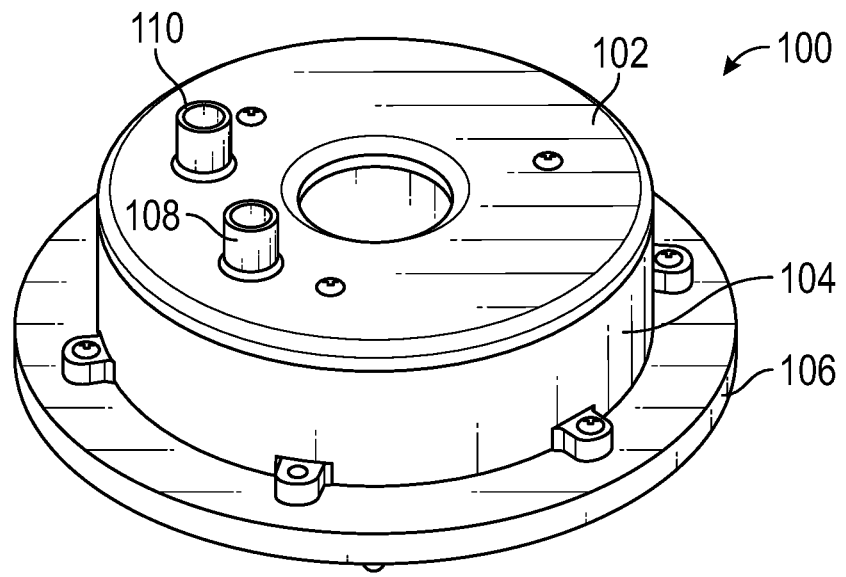
FIG. 1 depicts a perspective view of an embodiment of an irradiation chamber utilized with the currently disclosed gas irradiation system.
Figure 2:
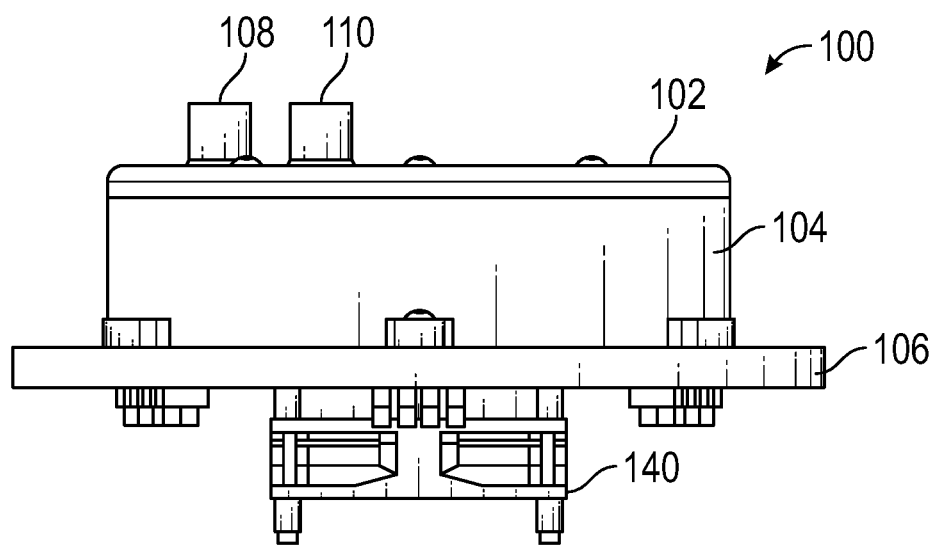
FIG. 2 depicts a front view of the irradiation chamber shown in FIG. 1.
Figure 3:
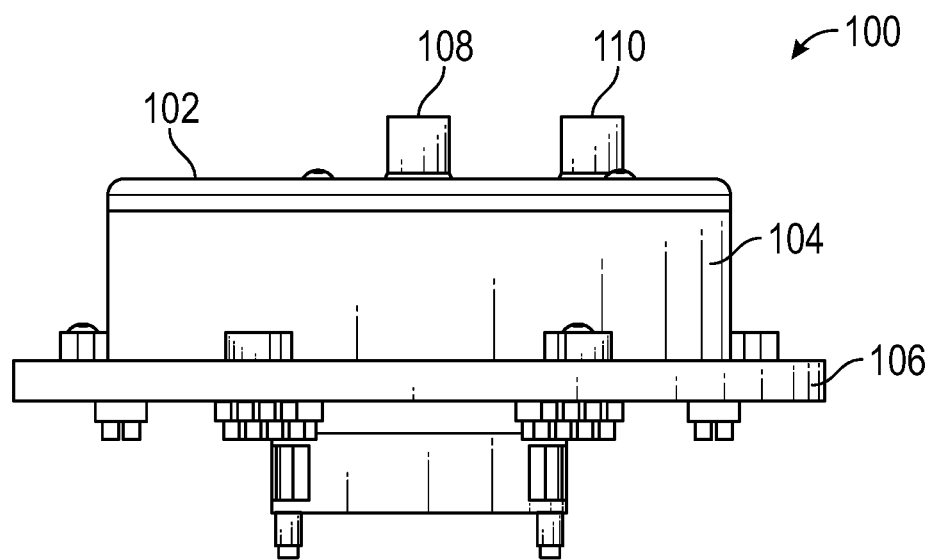
FIG. 3 depicts a side view of the irradiation chamber shown in FIG. 1.

Referring now to the Figures, FIG. 1 shows a perspective view of an embodiment of an irradiation chamber 100 which may be utilized with a gas irradiation system. While the gas irradiation system will typically be packaged as a self-contained unit for use by individuals, it is to be appreciated that components of the system may be utilized for irradiating gas streams for other applications. For example, multiple irradiation chambers 100 may be configured in parallel or in series to irradiate a gas stream for a room or building. The term "gas" as used in the present disclosure will most typically be referring to atmospheric air. However, embodiments of the present invention may be utilized to neutralize pathogens in any gas stream.

As shown in FIGS. 1 through 4, irradiation chamber 100 may be packaged in a generally cylindrical configuration. However, it is to be appreciated that non-cylindrical configurations compatible with the sequential irradiation compartment arrangement discussed below may also be utilized. Embodiments of the Irradiation chamber 100 may comprise a cover 102, a housing 104, a bottom member 106, an inlet 108 and an outlet 110. Cover 102 may be secured to housing 104 with screws or other attachment means. Likewise, housing 104 may be secured to bottom member 106 with threaded fasteners.

Figure 4:
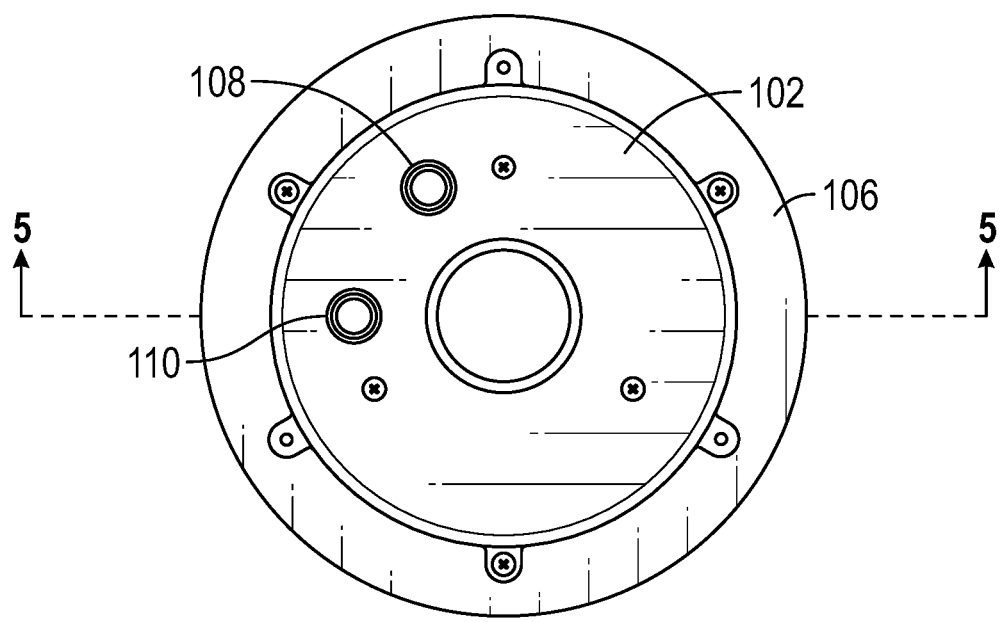
FIG. 4 depicts a top view of the irradiation chamber shown in FIG. 1.
Figure 5:
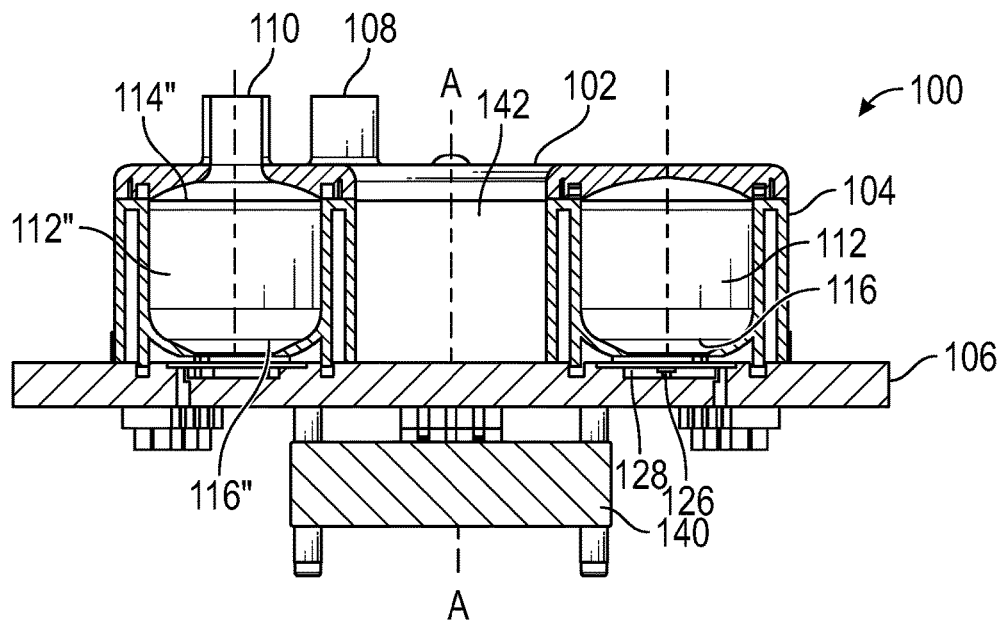
FIG. 5 shows a sectional view along line 5-5 of FIG. 4.
Figure 5A:
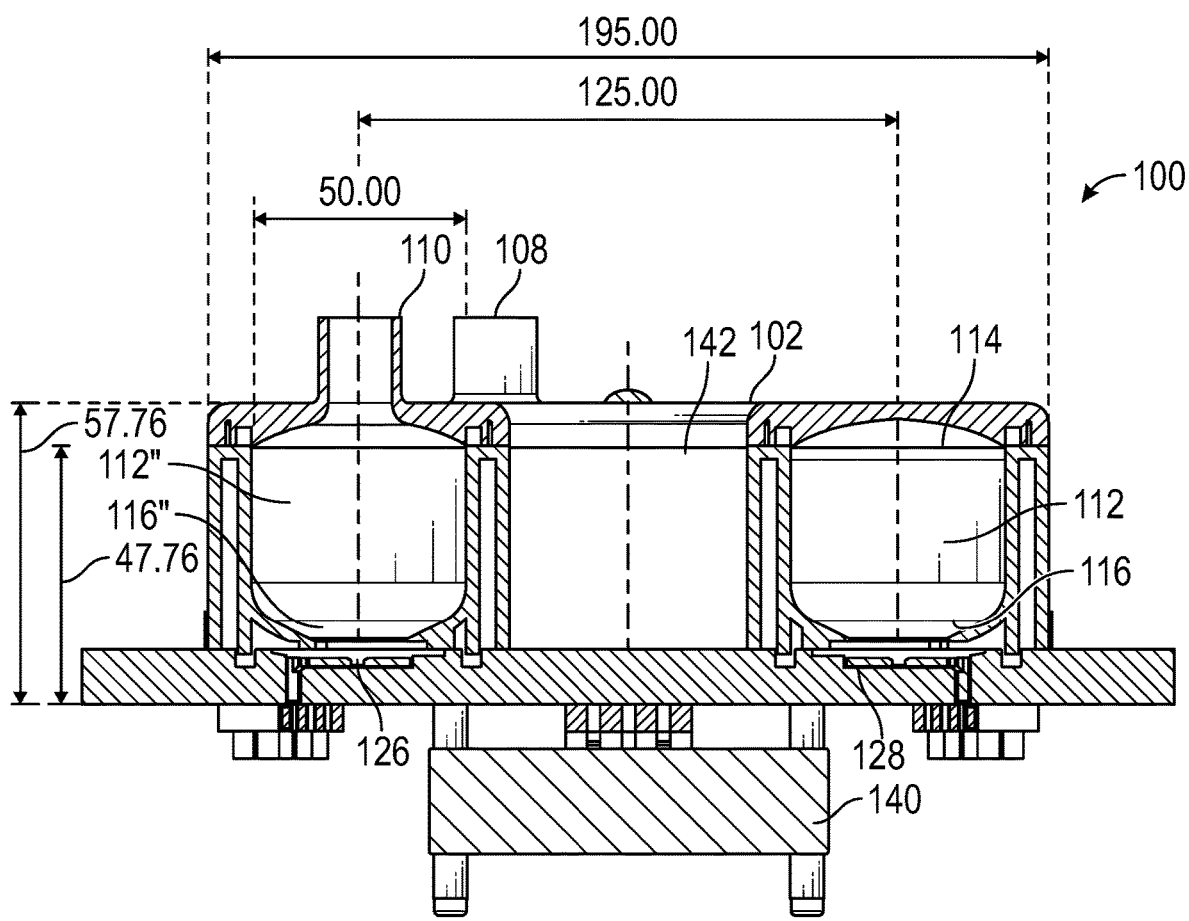
FIG. 5A shows a dimensioned sectional view for an embodiment of the irradiation chamber.
Figure 5B:
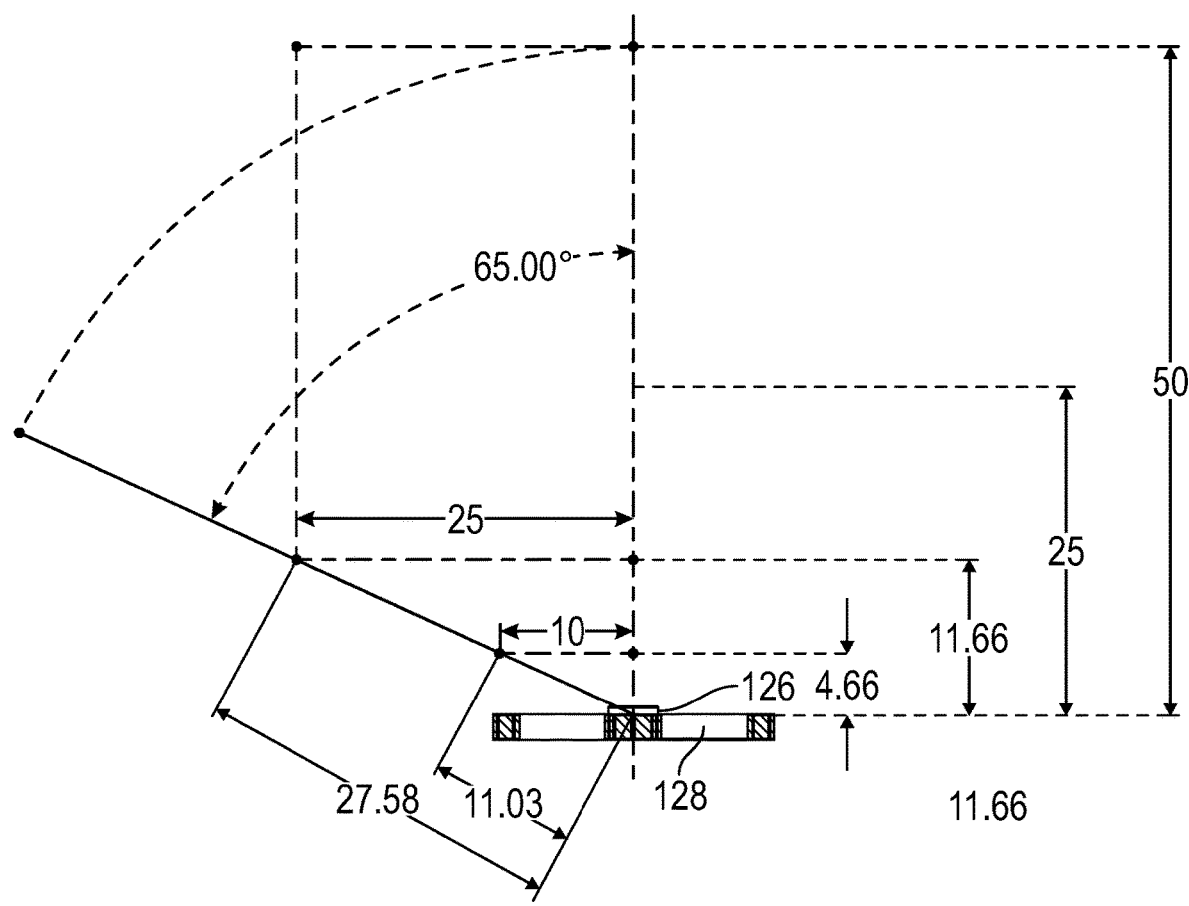
FIG. 5B depicts a dimensioned illumination profile within a chamber of an embodiment of an irradiation chamber.

FIGS. 5 and 5B show sectional views along line 5-5 of FIG. 4, showing the abutting attachment of housing 104 to bottom member 106 which creates flow passages between adjacent irradiation compartments 112, which are positioned circumferentially about axis A.

Irradiation chamber 100 may further comprise a cylindrical storage compartment 142 about which irradiation compartments are positioned circumferentially. Cylindrical storage compartment 142 may be utilized for storage of a power supply, such as a battery, for energizing the UV LEDS, the cooling fan, and/or a pressure differential apparatus utilized to provide gas flow through the irradiation chamber 100. FIGS. 5 and 5B show cooling fan 140 attached to the underside of bottom member 106. The dimensions (in millimeters) shown in FIG. 5A depict an irradiation chamber which is sized to provide an airflow rate suitable for the breathing requirements of a user, typically about 8 liters of air per minute.

FIG. 5B depicts a dimensioned (in millimeters) illumination profile for a UV LED 126 positioned at the bottom of a cylindrical irradiation compartment 112 within a chamber of an embodiment of an irradiation chamber, illustrating how a gas flowing through each of the irradiation compartments is sequentially exposed to the UVC radiation.

Figure 6:
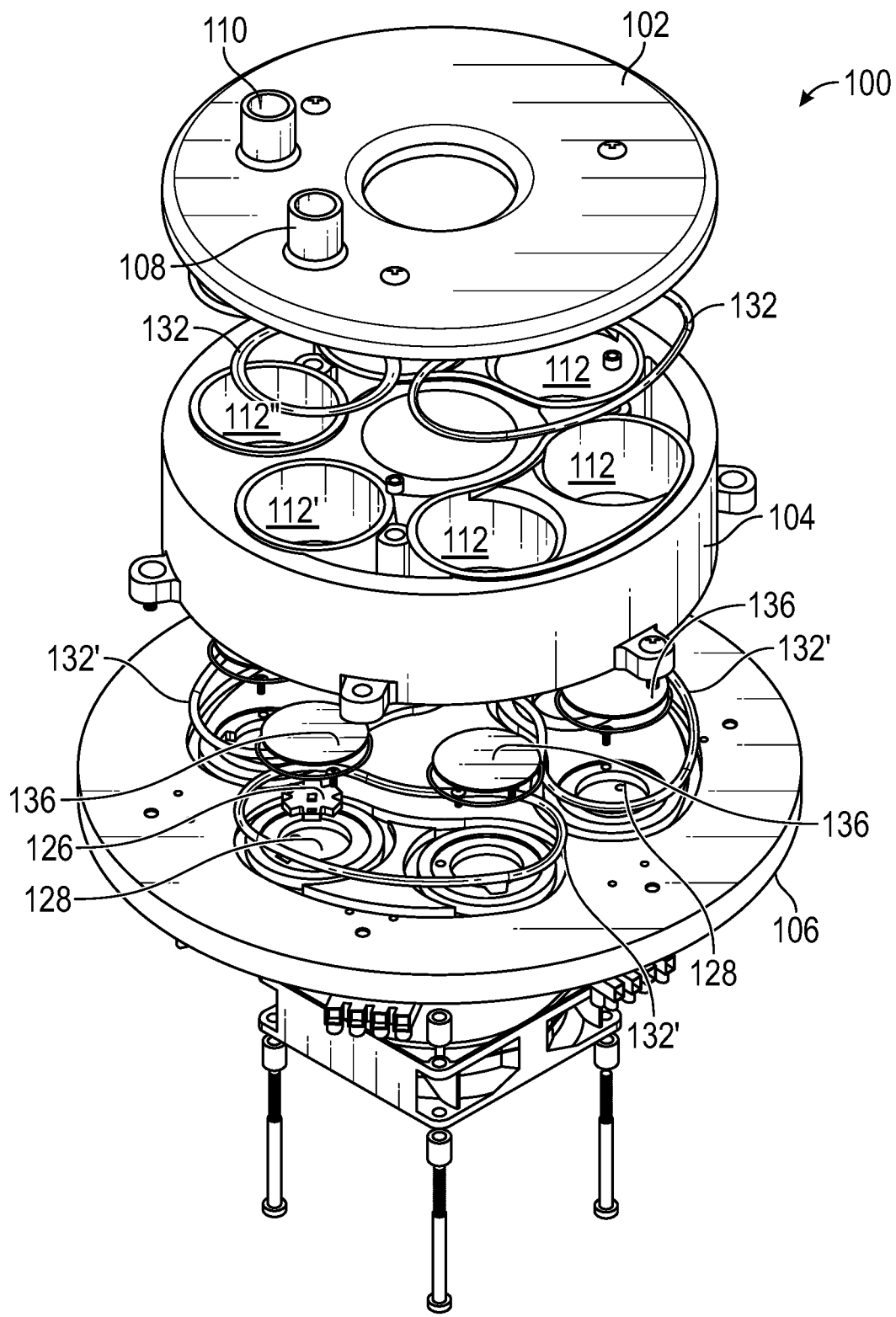
FIG. 6 depicts an exploded view of the irradiation chamber depicted in FIG. 1.

FIG. 6 depicts an exploded view of the irradiation chamber 100, showing an embodiment of an arrangement of the irradiation compartments 112 within housing 104 as per the present invention. The irradiation chamber 100 comprises a plurality of irradiation compartments 112 which are disposed circumferentially about a central axis A which may comprise also be the central axis for cylindrical storage compartment 142. The plurality of irradiation compartments 112 includes an inlet irradiation compartment 112' which receives an inflowing gas stream through inlet 108, and an outlet irradiation compartment 112" which discharges an outflowing gas stream through outlet 110. As shown in the figures, inlet irradiation compartment 112' and outlet irradiation compartment 112" are circumferentially adjacent to one another. The remaining intermediate irradiation compartments 112 are circumferentially disposed in the opposite circumferential direction between inlet irradiation compartment 112' and outlet irradiation compartment 112.

Figure 13:
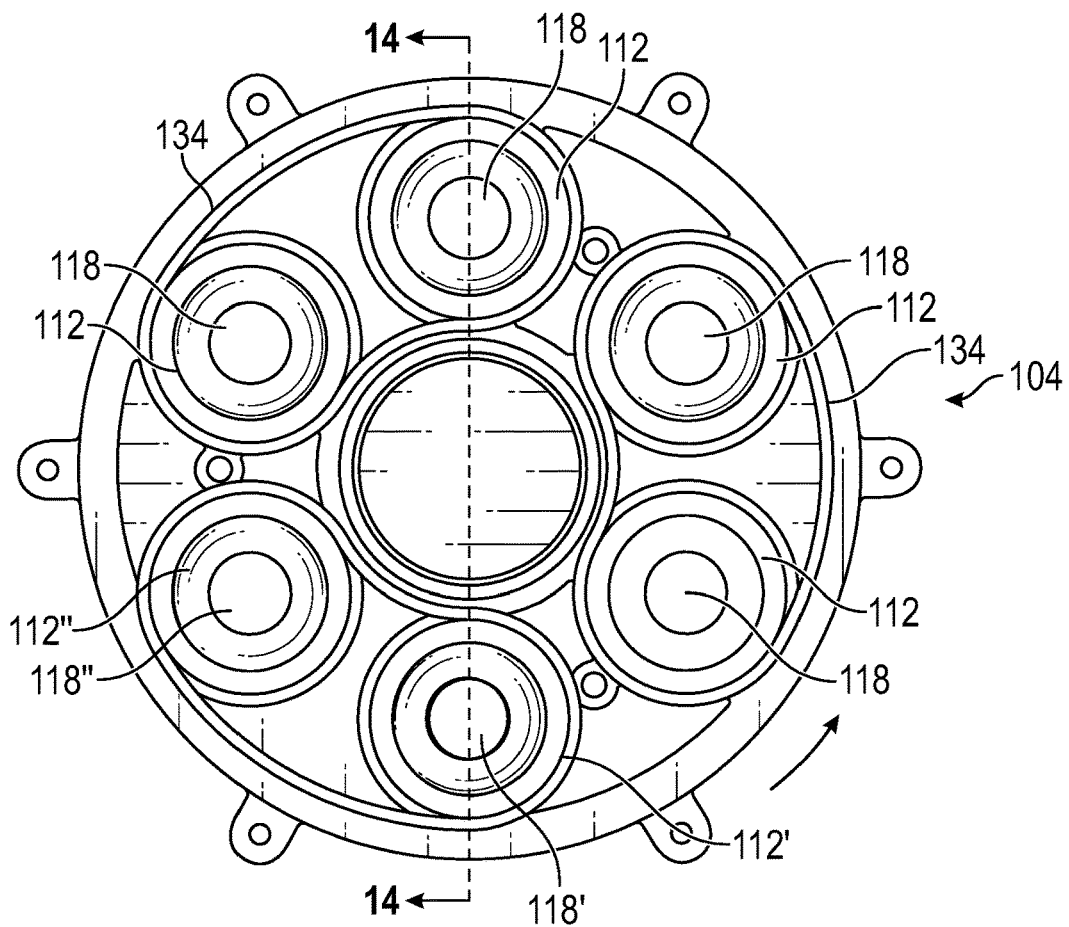
FIG. 13 shows a top view of the embodiment of the irradiation chamber body depicted in FIG. 12.
Figure 14:
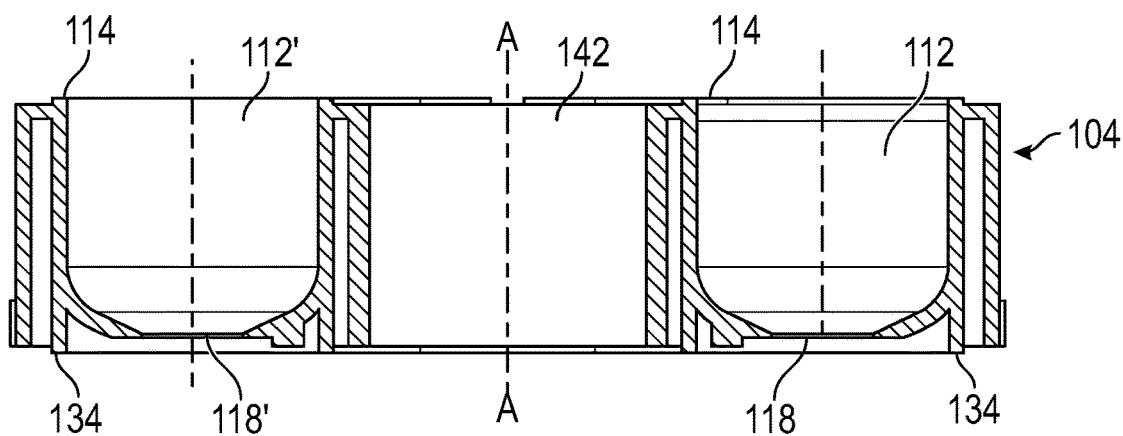
FIG. 14 is a sectional view of the irradiation chamber body taken along line 14-14 of FIG. 13.

A gas flowing through the irradiation chamber 100 flows sequentially through all of the irradiation compartments of irradiation chamber 100 starting at inlet irradiation compartment 112', through the plurality of intermediate irradiation compartments 112, into the outlet irradiation compartment 112" and flowing out of the irradiation chamber 100. The arrow on FIG. 13 shows the direction of flow beginning at irradiation compartment 112' as a gas stream flows counterclockwise through the intermediate irradiation compartments 112 and arriving at outlet irradiation compartment 112". The gas will typically be irradiated by a UV LED 126 as it passes through each irradiation compartment 112, thus decreasing the population of active pathogens sequentially. Each UV LED 126 may be covered by a protective lens 136 which will typically be fabricated from quartz.

Flow through irradiation chamber 100 may be reversed by changing the direction of the pressure differential applied to the irradiation chamber, such that the gas flow enters the irradiation chamber 100 through outlet 110 into outlet irradiation compartment 112" through intermediate irradiation compartments 112 into inlet irradiation compartment 112' and exiting through inlet 108.

Figure 12:
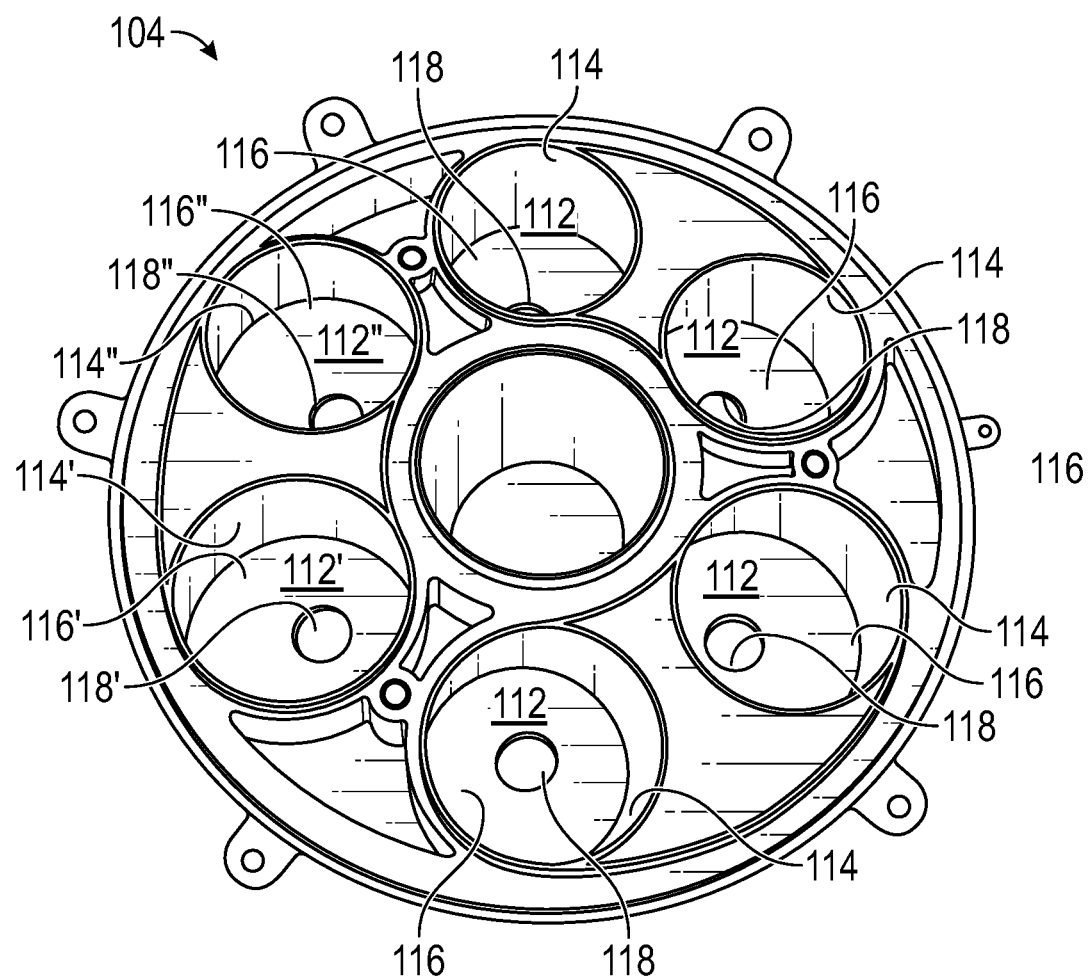
FIG. 12 depicts a top perspective view of an embodiment of the irradiation chamber body showing a configuration of the irradiation compartments disposed circumferentially about a central storage compartment.

As indicated in FIGS. 6 and 12, the irradiation compartments 112 may be in a cylindrical configuration. However, the irradiation compartments may be in a non-cylindrical configuration so long as the compartments are configured to provide for adequate UVC light dispersion within each compartment and the compartments are disposed circumferentially about a central axis and configured such that gas flows sequentially through all of the intermediate irradiation compartments 112 between the inlet irradiation compartment 112' and the outlet irradiation chamber 112"

Figure 15:
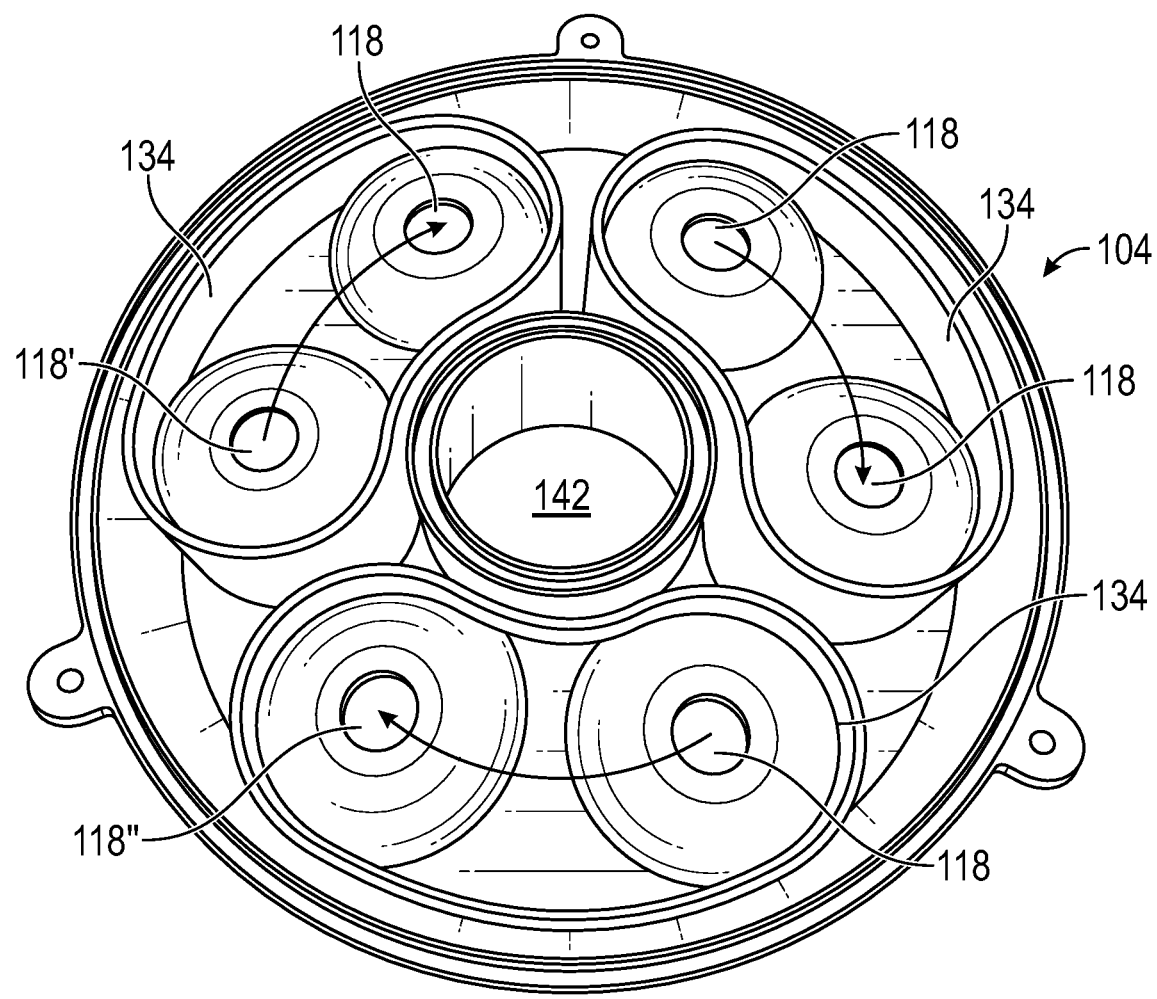
FIG. 15 depicts a bottom perspective view of the embodiment of the irradiation chamber body depicted in FIG. 12.

Each irradiation compartment 112 has an open top end 114 and a bottom end 116. Bottom end 116 is sealed except for an aperture 118 which penetrates through the bottom end 116 of each irradiation compartment 112 resulting in an opening in the underside of housing 104 as best shown in FIG. 15. As shown on FIG. 15, adjacent pairs of apertures 118 are enclosed on the underside of housing 104 by a seal wall 134 which may be generally configured in the shape of a kidney. A flow of gas which enters through inlet irradiation compartment 112' will flow out through aperture 118' and, because of the sealing of seal wall 134 by bottom member 106, will be directed to the circumferentially adjacent aperture 118 for entry into the circumferentially adjacent intermediate irradiation compartment 112. FIG. 15 indicates by the arrows the flow of gas between adjacent irradiation compartments until the gas flows into aperture 118" of outlet irradiation compartment 112". It is to be appreciated that in a reverse flow situation, the flow of gas will be in the opposite direction indicated by the arrows shown in FIG. 15.

Figure 7:
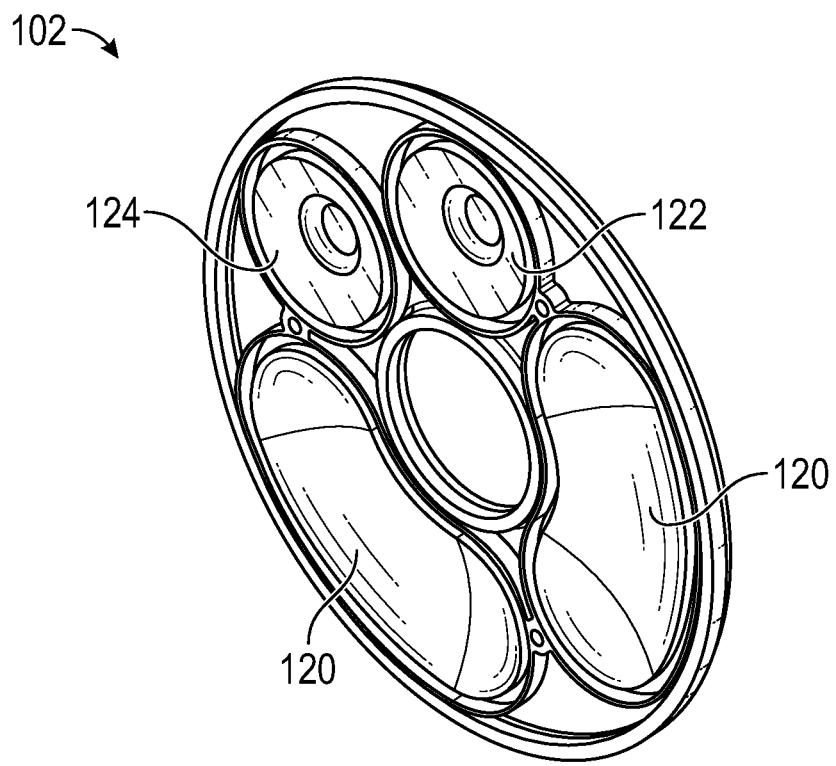
FIG. 7 depicts a perspective bottom view of an embodiment of a cover for the irradiation chamber depicted in FIG. 1.
Figure 8:
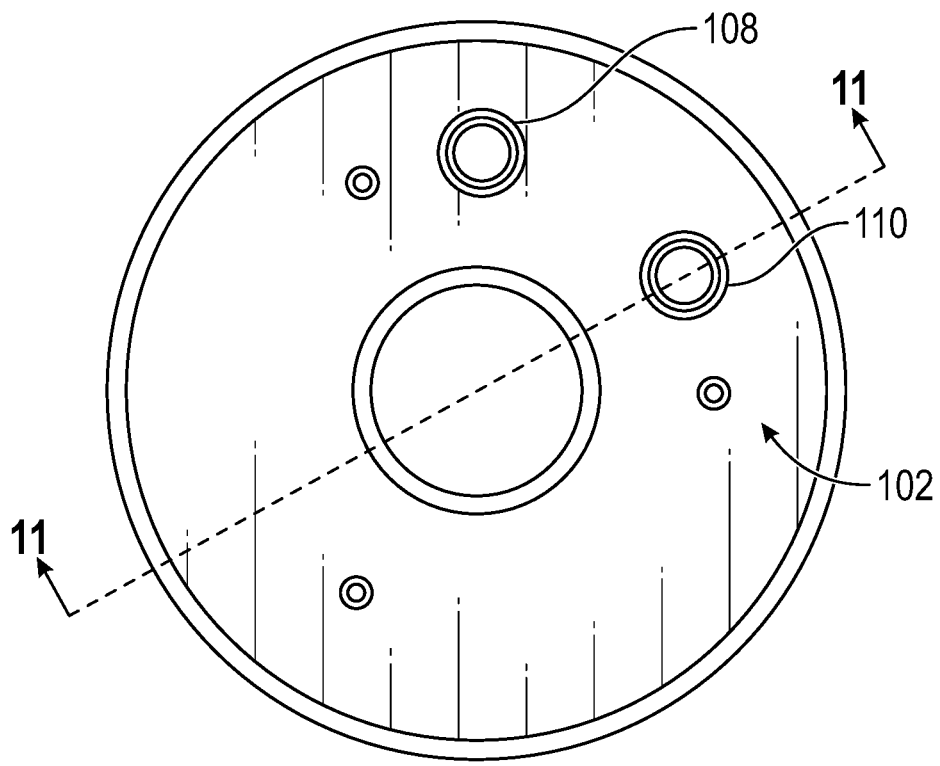
FIG. 8 depicts a top view of the cover for the irradiation chamber depicted in FIG. 7.

FIGS. 12 through 15 depict an embodiment of a housing 104 for the irradiation chamber 100. The open ends 114 of the irradiation compartments 112 are sealed by cover 102, an embodiment of which is shown in FIGS. 7 through 11. Cover 102 has an underside having flow channels 120 which allow gas flow between the top ends 114 of adjacent pairs of intermediate irradiation compartments 112. Such flow channels 120 are depicted in FIGS. 7 and 9. As also shown in FIGS. 7 and 9, the underside of cover 102 has an inflow chamber 122 which covers the top end 114' of inlet irradiation compartment 112' and an outflow chamber 124 which covers the top end 114" of outlet irradiation compartment 112". O-rings 132 may be utilized to increase the sealing around flow channels 120, the inflow chamber 122, the outflow chamber 114 which are utilized to convey gas flow between the open top ends 114 of adjacent irradiation compartments.

Figure 16:
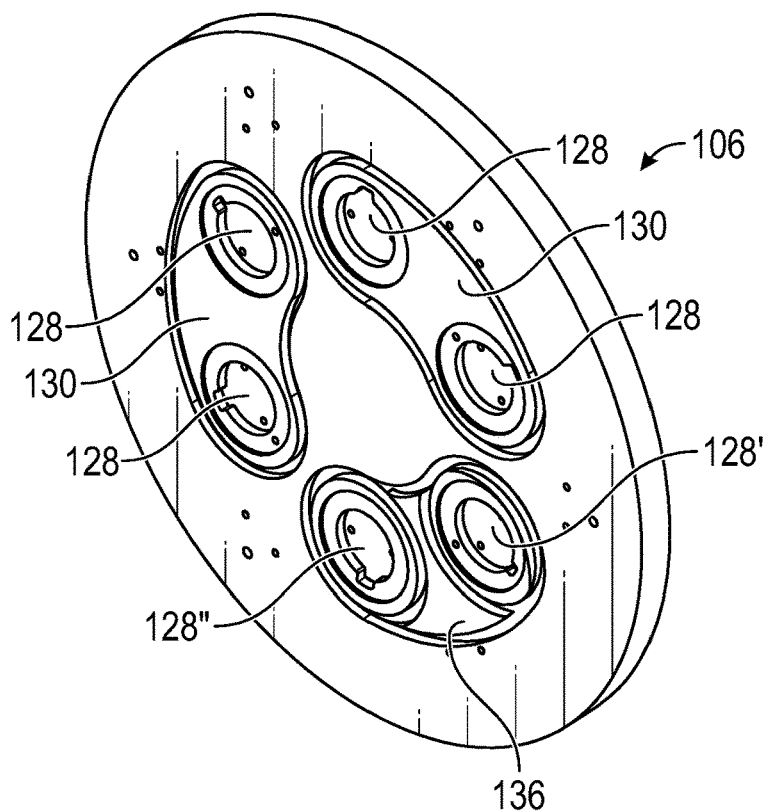
FIG. 16 is a top perspective view of a bottom member which seals against the bottom of the housing of the irradiation chamber.
Figure 17:
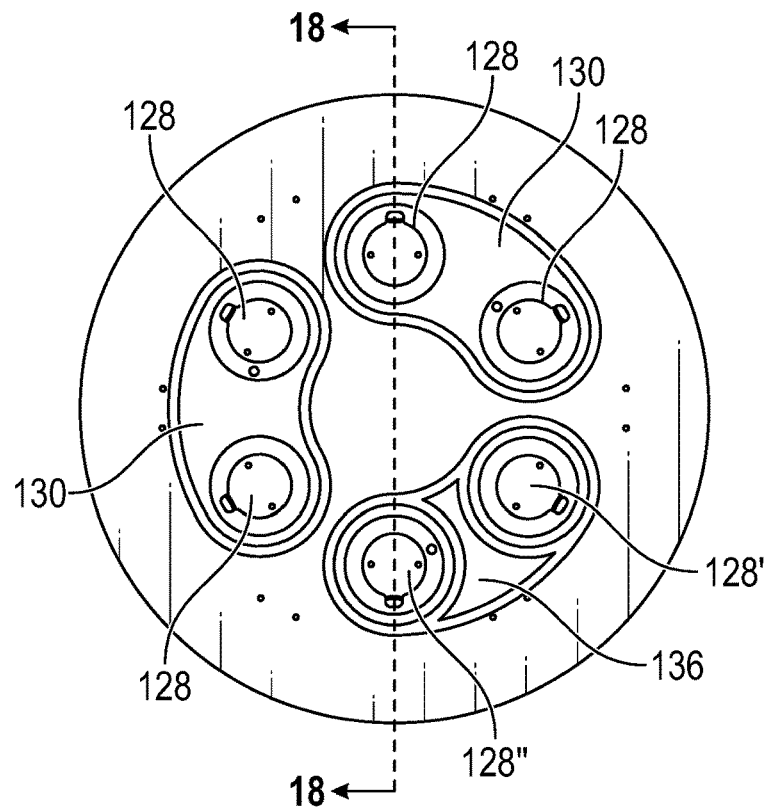
FIG. 17 is a top view of a bottom member which seals against the bottom of the housing of the irradiation chamber.
Figure 18:
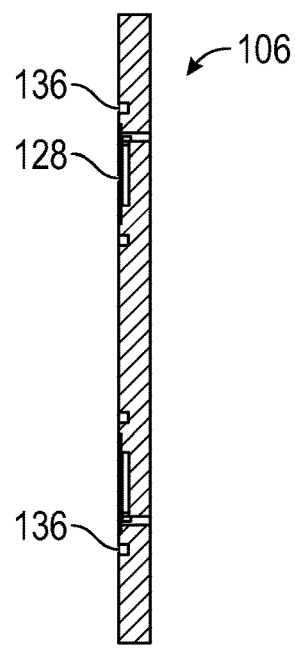
FIG. 18 is a sectional view of the bottom member taken along line 18-18 of FIG. 17.

The bottom ends 116 of irradiation compartments 112 are sealed off by bottom member 106 depicted in FIGS. 16 through 18. which seals against the bottom of housing 104 and seal walls 134. An embodiment of bottom member 106 is shown in greater detail in FIGS. 16 through 18. Contoured O-ring groove 130 defines a generally kidney-shaped footprint around adjacent seats 128. O-rings 132' are disposed within contoured O-ring grooves 130 to prevent gas flow except between adjacent irradiation compartments 112 in the sequence described above. Bottom member 106 is attached to housing 104 such that aperture 118' of the inlet irradiation compartment 112' is positioned directly above seat 128' shown in FIGS. 16-17. When so positioned, aperture 118" of the outlet irradiation compartment 112" will be positioned directly above seat 128". Because it is desirable that none of the gas entering inlet irradiation compartment 112' leak into outlet irradiation compartment 112", bottom member 106 may further comprise seal structure 136, which allows separate O-rings (not shown) to be placed around the seats 128', 128".

As suggested by the above description, when bottom member 106 is attached to the bottom of housing 104, seal walls 134 do not align with the generally kidney-shaped O-ring grooves around adjacent seats 128, but rather overlap.

Bottom member 106 may be utilized as a platform for UV LEDs 126 which may be seated in seats 128 of an upper side of bottom member 106. In order to redirect heat away from UV LEDs 126, bottom member 106 may be fabricated from a heat sink material such as copper or aluminum. Bottom member 106 may be fabricated with screw holes for retaining UV LEDs to the bottom member. Bottom member 106 may also have openings adjacent to seats 128 for running electrical leads and/or control wires to the UV LEDs 126.

Figure 19:
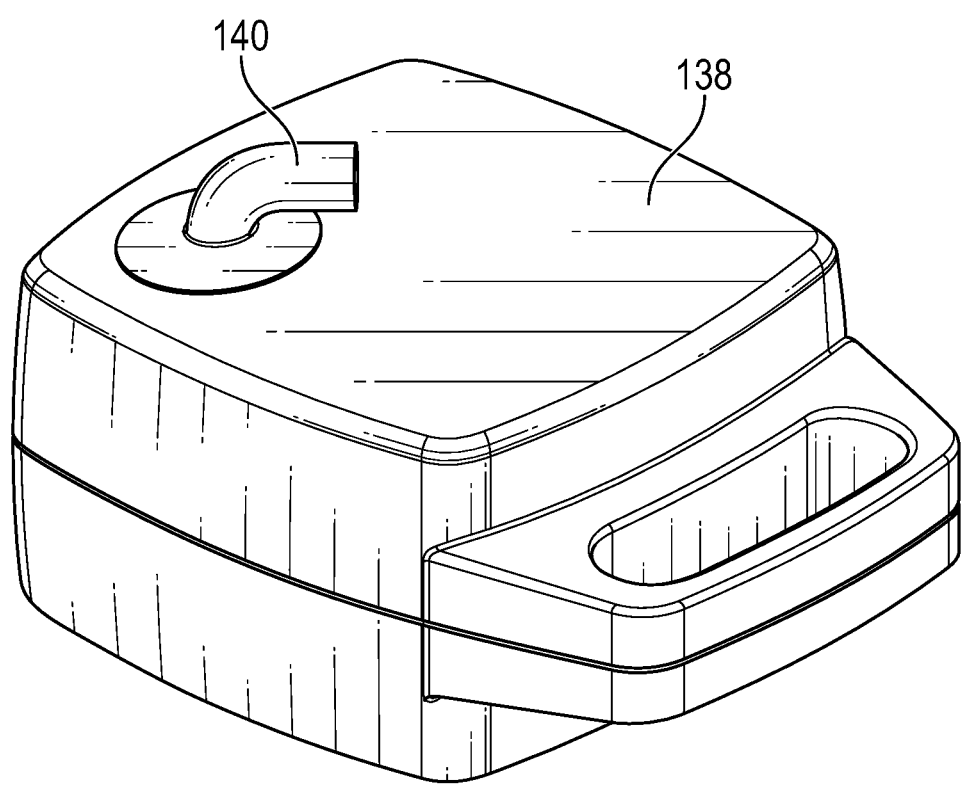
FIG. 19 depicts an embodiment of enclosure which may be utilized to house and transport the irradiation chamber.

FIG. 19 depicts a housing 138 which may be utilized to contain embodiments of irradiation chamber 100, showing an outlet 140 which receives irradiated gas from outlet 108 of the irradiation chamber. In addition to irradiation chamber 100, housing 138 may also contain a pressure differential apparatus, such as a positive pressure fan or vacuum fan for applying a pressure differential to irradiation chamber 100 to drive a gas flow through the irradiation chamber. Housing 138 may also contain a HEPA filter and filter carrier utilized to filter a gas entering the irradiation chamber. As indicated above, the flow direction through the irradiation chamber 100 may be reversed by changing the direction of the fan. In reverse flow operations, outlet 140 may be utilized to provide an inflow to the irradiation chamber.

Figure 20:
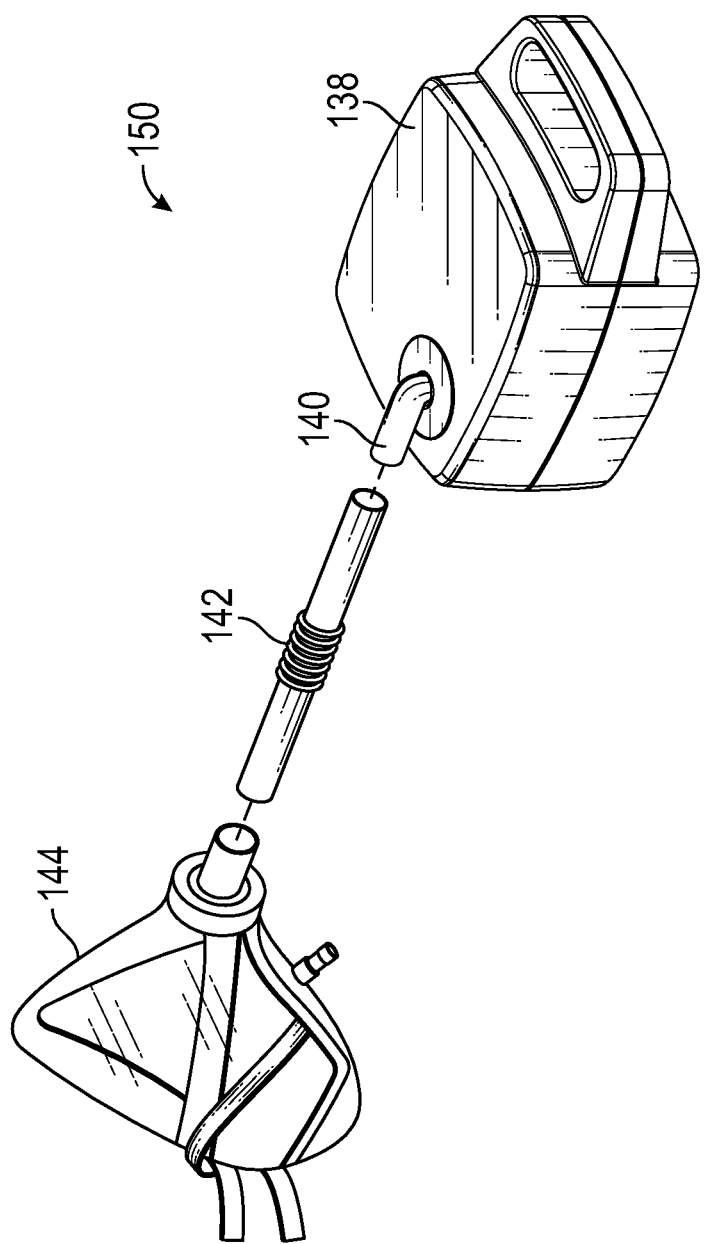
FIG. 20 depicts an embodiment of a personal breathing system of the presently disclosed invention.

FIG. 20 depicts an embodiment of a personal breathing system 150 of the presently disclosed invention which combines the irradiation chamber 100 contained within housing 138. A hose 142 is attached to outlet 140 of the housing 138 and a mask 144 attached to the hose. In reverse flow operation, exhalations containing pathogens may be directed into mask 144 and conveyed by hose 142 to the irradiation chamber 100 contained in the housing 138.

Having thus described the preferred embodiment of the invention, what is claimed as new and desired to be protected by Letters Patent includes the following:

1. A gas irradiation system comprising:
a housing member comprising a plurality of irradiation compartments disposed circumferentially about a central axis, the plurality of irradiation compartments comprising an inlet irradiation compartment, an outlet irradiation compartment, and a plurality of intermediate irradiation compartments disposed circumferentially between the inlet irradiation compartment and the outlet irradiation compartment, each irradiation compartment comprising an open top end and a bottom end, each bottom end comprising an aperture which penetrates the bottom end to form an opening for each irradiation compartment in an underside of the housing member, wherein the underside comprises a seal wall which encloses the openings of adjacent irradiation compartments, the seal wall providing a lower flow path between the adjacent irradiation compartments;
a cover which seals the open top ends of the irradiation compartments, wherein the cover has an underside having a flow channel configured to provide an upper flow path between the top ends of an adjacent pair of irradiation compartments;
a bottom member having an upper side configured to seal against the plurality of seal walls of the underside of the housing member;
a plurality of light emitting diodes wherein a light emitting diode is disposed within or adjacent to each of the apertures, wherein the light emitting diodes are configured to irradiate a flow of gas as the flow of gas passes through the irradiation compartments;
wherein the upper flow path and the lower flow path are configured such that the flow of gas passes sequentially through the inlet irradiation compartment, through the plurality of intermediate irradiation compartments, into the outlet irradiation compartment.

2. The gas irradiation system of claim 1 wherein each of the irradiation compartments are cylindrical.

3. The gas irradiation system of claim 2 wherein the light emitting diodes are mounted to the bottom member.

4. The gas irradiation system of claim 3 wherein the bottom member comprises a heat sink.

5. The gas irradiation system of claim 4 further comprising a heat dissipation fan attached to the bottom member.

6. The gas irradiation system of claim 1 further comprising a tube connected to the outlet irradiation compartment.

7. The gas irradiation system of claim 6 further comprising a face mask attached to the tube.

8. The gas irradiation system of claim 1 wherein the housing is cylindrical.

9. The gas irradiation system of claim 1 wherein the plurality of irradiation compartments are disposed about a cylindrical housing.

10. The air irradiation system of claim 9 wherein the power source is disposed within the cylindrical housing.

11. A gas irradiation system comprising:
a housing comprising a central axis, the housing further comprising a plurality of irradiation compartments, the plurality of irradiation compartments individually disposed in a circumferential configuration about the central axis, the plurality of irradiation compartments comprising an inlet compartment and a circumferentially adjacent outlet compartment on a first side of the inlet compartment, and a plurality of intermediate compartments extending circumferentially between a second side of the inlet compartment and the outlet compartment; and
a plurality of ultraviolet light emitting diodes, wherein each of the plurality of irradiation compartments comprises at least one of the ultraviolet light emitting diodes, wherein each of the ultraviolet light emitting diodes of the plurality of ultraviolet light emitting diodes is configured to progressively irradiate a flow of gas as it sequentially flows through the inlet compartment, the intermediate compartments, and the outlet compartment.

12. The gas irradiation system of claim 11 wherein each of the plurality of irradiation compartments is cylindrical.

13. The gas irradiation system of claim 11 further comprising a bottom member which attaches to a bottom end of each of the irradiation compartments of the plurality of irradiation compartments, wherein a flow channel is defined between the bottom ends of adjacent irradiation compartments and the bottom member, the flow channel configured to direct the flow of gas between adjacent irradiation compartments.

14. The gas irradiation system of claim 13 wherein the plurality of light emitting diodes are mounted to the bottom member.

15. The gas irradiation system of claim 11 wherein each of the plurality of irradiation compartments comprises a top and a bottom, the plurality of irradiation compartments configured such that the flow of gas sequentially flows: (i) from the top of the inlet compartment to the bottom of the inlet compartment, (ii) into the bottom of a circumferentially adjacent first intermediate irradiation compartment to the top of the first intermediate irradiation compartment, (iii) into the top of a circumferentially adjacent second intermediate irradiation compartment to the bottom of the second intermediate irradiation compartment, (iv) into the bottom of a circumferentially adjacent third intermediate irradiation compartment to the top of the third intermediate irradiation compartment, (v) into the top of a circumferentially adjacent fourth intermediate irradiation compartment to the bottom of the fourth intermediate irradiation compartment, and (vi)

into the bottom of the circumferentially adjacent outlet compartment to the top of the outlet compartment, the flow of gas exiting the outlet compartment through an outlet.

16. The gas irradiation system of claim 11 further comprising a tube connected to the outlet compartment.

17. The gas irradiation system of claim 16 further comprising a face mask attached to the tube.

18. The air irradiation system of claim 11 wherein the housing is in a cylindrical configuration.

19. A method of irradiating a stream of gas comprising the following steps:

directing the gas into an inlet of a housing, the housing comprising a plurality of irradiation compartments, the plurality of irradiation compartments individually disposed in a circumferential configuration about a central axis, the plurality of irradiation compartments comprising an inlet compartment and a circumferentially adjacent outlet compartment on a first side of the inlet compartment, and a plurality of intermediate compartments extending circumferentially between a second side of the inlet compartment and the outlet compartment;

energizing a plurality of ultraviolet light emitting diodes, wherein each of the plurality of irradiation compartments comprises at least one of the ultraviolet light emitting diodes, wherein each of the ultraviolet light emitting diodes of the plurality of ultraviolet light emitting diodes is configured to progressively irradiate the flow of gas as the gas sequentially flows through the inlet compartment, the intermediate compartments, and the outlet compartment resulting in flow of an irradiated gas stream to an outlet of the outlet compartment; and directing the irradiated gas stream to a mask.

20. The method of claim 19 wherein each of the plurality of irradiation compartments comprises a top and a bottom, the plurality of irradiation compartments configured such that the flow of gas sequentially flows: (i) from the top of the inlet compartment to the bottom of the inlet compartment, (ii) into the bottom of a circumferentially adjacent first intermediate irradiation compartment to the top of the first intermediate irradiation compartment, (iii) into the top of a circumferentially adjacent second intermediate irradiation compartment to the bottom of the second intermediate irradiation compartment, (iv) into the bottom of a circumferentially adjacent third intermediate irradiation compartment to the top of the third intermediate irradiation compartment, (v) into the top of a circumferentially adjacent fourth intermediate irradiation compartment to the bottom of the fourth intermediate irradiation compartment, and (vi) into the bottom of the circumferentially adjacent outlet compartment to the top of the outlet compartment, the flow of gas exiting the outlet compartment through an outlet.

* * * * *